(12) United States Patent
Subirana Cleric et al.

(10) Patent No.: US 11,027,171 B2
(45) Date of Patent: Jun. 8, 2021

(54) TENSILE FORCE SENSOR FOR RECORDING AND MONITORING PHYSICAL EXERCISE

(71) Applicant: ESTEL, S.L., Barcelona (ES)

(72) Inventors: Montserrat Subirana Cleric, Barcelona (ES); Juan Jose Ramos Castro, Barcelona (ES); Sergio Rodriguez Jimenez, Barcelona (ES); Gerard Moras Feliu, Barcelona (ES); Ramon Bragos Bardia, Barcelona (ES); Miguel Angel Garcia Gonzalez, Barcelona (ES)

(73) Assignee: ESTEL, S.L., Barcelona (ES)

( * ) Notice: Subject to any disclaimer, the term of this patent is extended or adjusted under 35 U.S.C. 154(b) by 0 days.

(21) Appl. No.: 16/345,190

(22) PCT Filed: Oct. 25, 2017

(86) PCT No.: PCT/ES2017/000142
§ 371 (c)(1),
(2) Date: Apr. 25, 2019

(87) PCT Pub. No.: WO2018/078197
PCT Pub. Date: May 3, 2018

(65) Prior Publication Data
US 2019/0275371 A1 Sep. 12, 2019

(30) Foreign Application Priority Data
Oct. 25, 2016 (ES) .............................. ES201631367

(51) Int. Cl.
*A63B 24/00* (2006.01)
*A61B 5/00* (2006.01)
*A63B 23/00* (2006.01)

(52) U.S. Cl.
CPC ........ *A63B 24/0003* (2013.01); *A61B 5/6895* (2013.01); *A63B 23/00* (2013.01); *A63B 2220/51* (2013.01); *A63B 2225/50* (2013.01)

(58) Field of Classification Search
CPC . A63B 24/0003; A63B 23/00; A63B 2220/51; A63B 2225/50; A63B 21/026;
(Continued)

(56) References Cited

U.S. PATENT DOCUMENTS 3,937,075 A     2/1976  Landvogt
4,235,439 A *  11/1980  De Donno ........... A63B 21/015
                                                       188/75
(Continued)

FOREIGN PATENT DOCUMENTS

EP        0227597 A1    7/1987
EP        0083568 B1   12/1990
(Continued)

*Primary Examiner* — Garrett K Atkinson
(74) *Attorney, Agent, or Firm* — Bycer Law, PLC; Matthew L. Bycer

(57) ABSTRACT

The tensile force sensor comprises at least one strain gauge in a tension piece comprising a central rectilinear segment and two folds at an angle, significantly thicker than the central rectilinear segment. The strain gauge is arranged in said central rectilinear segment in such a manner that a traction force on the fastening ends of the tension piece results in a U-shaped buckling of the central rectilinear segment. The invention also comprises a processing module connected to the strain gauge, adapted to detect and process as data the elastic deformations caused in the central rectilinear segment by the longitudinal stresses generated by traction on the fastening ends of the tension piece. The invention allows a portable and low cost wireless sensor to be produced.

9 Claims, 4 Drawing Sheets

(58) Field of Classification Search
CPC ..... A63B 24/0062; A63B 23/129; G01L 1/22;
G01L 5/101; G01L 5/102; G01L 5/045;
A61B 5/6895
See application file for complete search history.

(56) References Cited

U.S. PATENT DOCUMENTS

| | | | |
|---|---|---|---|
| 4,307,608 A | 12/1981 | Useldinger et al. | |
| 4,728,102 A * | 3/1988 | Pauls ................ | A63B 21/015 482/118 |
| 4,785,673 A | 11/1988 | Aumard | |
| 5,090,421 A | 2/1992 | Wagoner | |
| 5,090,694 A * | 2/1992 | Pauls ................ | A63B 21/015 482/118 |
| 5,399,136 A * | 3/1995 | Bart .................. | A63B 21/227 446/242 |
| 5,529,552 A * | 6/1996 | Biedermann ....... | A63B 21/153 482/111 |
| 5,643,157 A * | 7/1997 | Seliber .............. | A63B 21/0058 482/112 |
| 6,033,283 A * | 3/2000 | Chen ................. | A61C 15/041 446/253 |
| 6,283,899 B1 * | 9/2001 | Charnitski ......... | A63B 21/15 482/102 |
| 6,436,006 B1 * | 8/2002 | Zemlyakov ........ | A63B 21/0083 482/112 |
| 7,497,807 B2 * | 3/2009 | Neff .................. | A63B 22/0694 482/8 |
| 7,497,812 B2 * | 3/2009 | Neff .................. | A63B 21/008 482/51 |
| 7,922,635 B2 * | 4/2011 | Lull .................. | A63B 21/00 482/100 |
| 9,314,659 B2 * | 4/2016 | Gvoich .............. | A63B 21/062 |
| 9,498,666 B1 * | 11/2016 | Boatwright ....... | A63B 23/03525 |
| 10,143,880 B1 * | 12/2018 | Boatwright ........ | A63B 21/075 |
| 10,188,890 B2 * | 1/2019 | Olson ................ | A63B 21/154 |
| 10,252,109 B2 * | 4/2019 | Watterson .......... | A63B 21/072 |
| 10,426,989 B2 * | 10/2019 | Dalebout ........... | A63B 22/0007 |
| 10,441,840 B2 * | 10/2019 | Dalebout ........... | A63B 21/0552 |
| 10,449,416 B2 * | 10/2019 | Dalebout ........... | A63B 22/0007 |
| 2014/0148317 A1 | 5/2014 | Mutch et al. | |

FOREIGN PATENT DOCUMENTS

| | | |
|---|---|---|
| ES | 2347516 A1 | 10/2010 |
| ES | 1079025 U | 4/2013 |
| GB | 1440857 | 6/1976 |
| GB | 2528234 A | 1/2016 |
| WO | WO2014125424 A1 | 8/2014 |

* cited by examiner

TENSILE FORCE SENSOR FOR RECORDING AND MONITORING PHYSICAL EXERCISE

CLAIM OF PRIORITY

The present application includes subject matter disclosed in and claims priority to Spanish Patent Application No. P201631367 filed on Oct. 25, 2016; and Patent Cooperation Treaty (PCT) application Serial No. PCT/ES2017/000142, entitled "Traction Force Sensor for Recording and Monitoring Physical Exercise" filed Oct. 25, 2017, describing an invention made by the present inventors, and herein incorporated by reference.

OBJECT OF THE INVENTION

The invention is included in the sector of physical activity and athletic training, in the fields of both health and high performance.

The present invention relates to a tensile force sensor for the recording and monitoring of physical activity, equipped with a strain gauge with sufficient exactitude, minimal weight and low cost, for the monitoring and analysis of physical activity.

The sensor of the present invention may also be applicable for other uses, such as the measurement of distortions in load-bearing structures, the weighing of articles, the dosing of materials, etc.

STATE OF THE ART

There exist various solutions for the measurement of mechanical tension, although all of these are based on the transduction of the force into a distortion to be estimated subsequently by means of resistive, capacitive, inductive or piezoelectric sensors.

In the physical activity and sports sectors, and in athletic training, there exist several types of force transducers. Some devices are integrated in stationary machinery of considerable size, and are therefore not portable, for the monitoring of forces applied in the specific movements for which the machine has been designed.

There also exist portable sensors for the assessment of the force exerted by the human body or by parts of the same. For example, patent EP0083568B1 discloses a classic manual one-way compression force sensor, based on strain gauges.

Similarly, U.S. Pat. No. 5,090,421 discloses a machine for use in muscular assessment tests comprising a force transducer based on strain gauges, to provide precise deflection readings, including force applied in different directions. This machine is connected via a cable to an external device, a computer, which collects and displays the force data obtained.

Document U.S. Pat. No. 4,307,608A discloses a machine which enables the digital viewing of the value of the muscular force exerted in compression or traction, and consisting of a console with an electronic circuit which receives the output signal from an independent load cell which is connected via a cable to the console and is able to transform the elastic distortions of a rigid article into electrical changes by means of the use of strain gauges.

The patent application document WO02014125424A1 discloses a system for training under suspension which may also include a sensor for the registration of the force (supposedly tractional) generated during the exercises with suspension of the body or of parts of the same, and which interacts with the user or the trainer by means of a graphic or audio interface. Furthermore, the sensor for the recording of the force may include an accelerometer to determine the movements or the vibrations, or other types of supplementary external sensors such as ECG, EMG, heart rate loggers, etc. The sensors may interact with computers, mobile devices or tablets.

Application US20140148317A1 describes a system for muscular exercise comprising a clip for the attachment of elastic bands to a fixed point, and sheaths or sleeves for their attachment to cylindrical parts of the body, such as a leg or an arm. The sleeve features at least one attachment means for its anchoring to the elastic bands. The shape of one part of the clip enables the elastic band to be rolled up spirally or helicoidally. The clip may include a system for the measurement of the tensile load, for example a strain gauge, to measure the peak or average force generated in the elastic band.

Patent application GB2528234A, considered to be the "closest prior art", discloses a sensor device comprised of two casings, the right casing and the left casing, each containing a force sensor based on a load cell, enabling the separate measurement of the force exerted on the left and right sides. Both casings present anchor points for their attachment to external resistance systems such as rubber straps, pulleys, etc. Both casings are fixed together by means of a pivoting system or hinge which enables them to rotate and to be aligned with the direction of the tensile force to which the system is subjected. A final attachment point enables the anchoring of the device to any fixed point. The records provided by the load cells may be wirelessly sent to a remote device such as a computer or a smartphone. A software associated with the device enables the analysis of the records, and the assessment of the activity performed by the user, and the suggestion of different exercises to improve his state of fitness.

As may be inferred from the description of the closest prior art, the greatest drawback, generally speaking, is the construction of a sensor system with a reduced cost and minimum weight (<0.175 kg), but sufficiently accurate (resolution of the measurement <0.3 kg) and sufficient nominal load capacity (up to 250-300 kg) to monitor wirelessly the levels of force exerted during actions and exercises typical of strength training. Furthermore, document GB2528234A discloses a sensor which requires two strain gauges, this entailing the drawback of making the device more costly and its management more complex.

The use of commercial load cells is ruled out due to their cost being too high to fulfil the requirements of the application, and to their not adapting to the functional requirements of minimum weight and reduced size.

Another more specific drawback is the design of a tensioner with a suitable shape, material and dimensions to fulfil, at a low production cost, the requirements of exactitude in measurement, minimum weight and sufficient functionality.

EXPLANATION OF THE INVENTION

The object of the present invention is to solve the aforementioned problems and drawbacks. To this end, the object of this invention, as claimed in claim 1, is a tensile force sensor for the recording and monitoring of physical exercise, of the type described at the commencement herein, which is characterised essentially in that it comprises a tensioner (which performs the primary force-distortion transduction), made from a hard material with a particular constant of elasticity and which comprises a straight central segment and two angled bends, significantly thicker than the straight central segment, a strain gauge being disposed on said straight central segment. A tensile force at the affixing extremities of the tensioner is transformed into a U-shaped distortion of the straight central segment, this being measured by the strain gauge.

In claims 2 et seq., preferred embodiments of the present invention are described.

Therefore, the invention features a number of characteristics which are both innovative and advantageous, particularly as it enables the manufacture in a single item of sensors of reduced weight, reduced size and lightweight materials, in comparison with those of the state of the art, differing from those with similar functions already in existence, among other reasons, in that it may be manufactured by means of stamping, reducing the need for mechanisation.

The sensor system of the present invention combines many features, based on high precision, a high maximum load capacity and high functionality at a reduced cost, enabling the wireless monitoring of the levels of tensile force exerted during dynamic and static actions and exercises typical of strength training.

Another competitive advantage is the absence in the market, to date, of low-cost tensile force sensors such as that of the present invention, enabling the control of the device and the management of the data obtained by means of applications for mobile telephones, tablets or other mobile devices.

BRIEF DESCRIPTION OF THE DRAWINGS

A detailed description is made below of a preferred embodiment of the wireless tensile force sensor of the present invention; for the better understanding thereof a set of drawings is attached, provided merely for illustrative and not limitative purposes, wherein.

DETAILED DESCRIPTION OF A PREFERRED EMBODIMENT OF THE INVENTION

In said drawings, the constitution and modus operandi of the force sensor system of the present invention may be seen.

Figure 1:
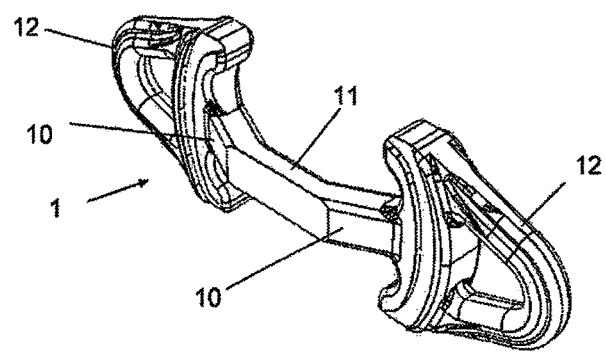
FIG. 1 is a perspective view of a preferred design of the tensioner of the sensor of the present invention.
Figure 2:
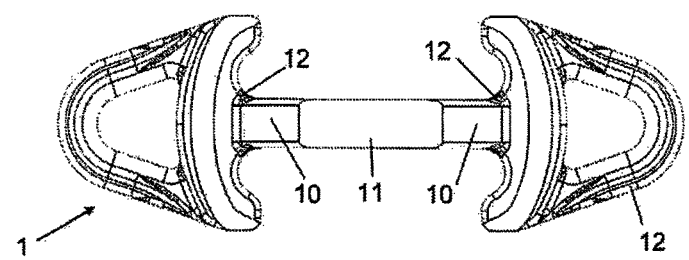
FIG. 2 is an upper plan view of the drawing of the tensioner in FIG. 1.
Figure 3:
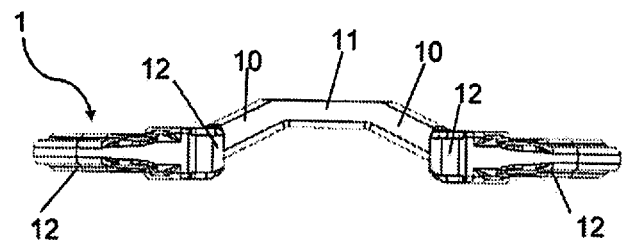
FIG. 3 is a profile view of the tensioner in FIG. 1, when not under stress.
Figure 4:
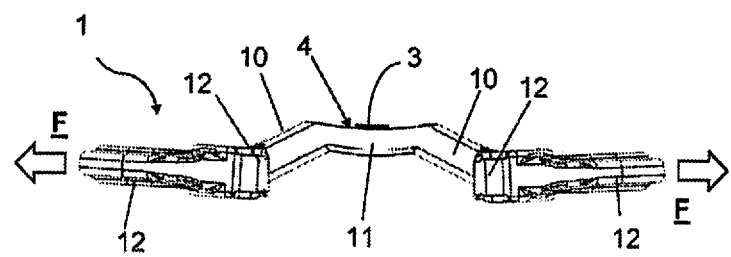
FIG. 4 is an analogous view, but with a tensile force (F), indicated by the arrows, exerted on the tensioner and wherein the distortion of the straight central segment of the tensioner of the present invention may be seen.
Figure 5:
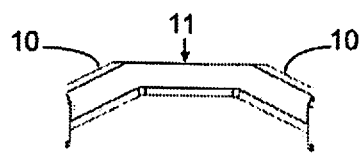
FIG. 5 is a detailed profile view of said straight central segment, with the two angled bends of the tensioner, significantly thicker than the straight central segment. Note that the straight central segment is the part destined for the attachment of the strain gauge.
Figure 6:
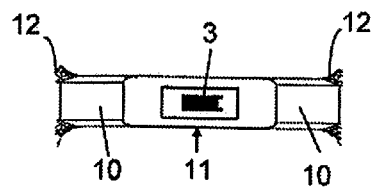
FIG. 6 is an upper plan view of the straight central segment in FIG. 5.

The sensor system of the present invention consists of a tensioner (1) which carries out the primary force-distortion transduction, and which consists of a simple body of hard material with a particular constant of elasticity and which may be obtained by means of stamping, based on a straight central segment (11) with two angled bends (10), significantly thicker than the straight central segment (11). This enables a tensile force at the affixing extremities (12) of the tensioner (1) to be transformed into a U-shaped distortion (4) at the straight central segment (11), there being, affixed to said straight central segment (11) a single distortion sensor, such as a strain gauge (3), connected in turn to a processing module (5) able to detect and to process in data the slight elastic distortion of said straight central segment (11) due to the longitudinal effort generated by the traction of the affixing extremities (12) of the tensioner (1). In FIG. 6 an example is portrayed wherein the strain gauge is installed on the upper side of the straight central segment (11), although the case has been considered wherein it may be installed on the lower side, or even on both sides (examples not portrayed in the drawings).

Furthermore, the two affixing extremities (12) of the tensioner (1) of the sensor system feature spaces destined for the attachment, by conventional anchoring means such as carabiners, to conventional machines and resistance systems for physical training with external loads, such as resistance machines with gravitational pulleys, elastic bands or rigid straps for training under suspension, among others.

In accordance with an essential characteristic of the present invention, the force sensor system comprises a processing module (5) (FIG. 8) connected to the strain gauge (3), adapted to detect and to process in data the elastic distortions caused in the straight central segment (11) by the longitudinal effort generated by the traction of the affixing extremities (12) of the tensioner (1). The processing module (5) may be disposed near the straight central segment (11) of the tensioner (1).

Figure 8:
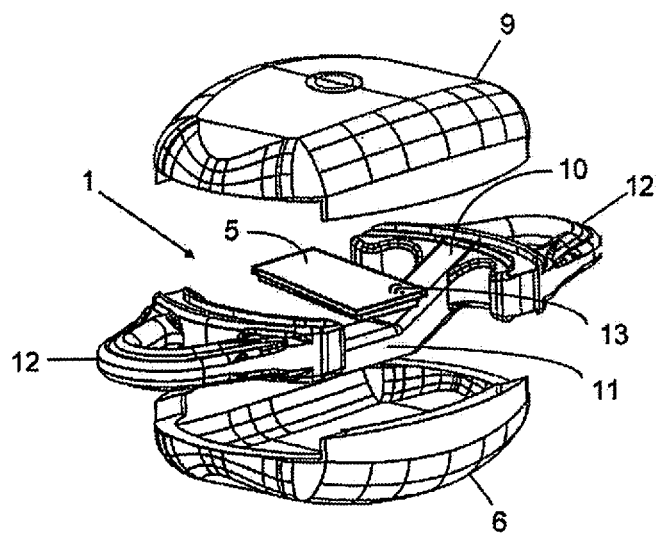
FIG. 8 is an exploded view of the tensioning system in FIG. 7, with the casing removed, wherein the processing module is portrayed and the wireless transmitter module may be seen.

In FIG. 8 it may be seen that the system also features a wireless transmitter module (13), which sends the data concerning the elastic distortions to an external device, such as a smartphone or tablet, or to a server which processes the same. This processing is performed preferably by a specific app to present the information to the user and to save the recorded results in said external device.

Figure 7:
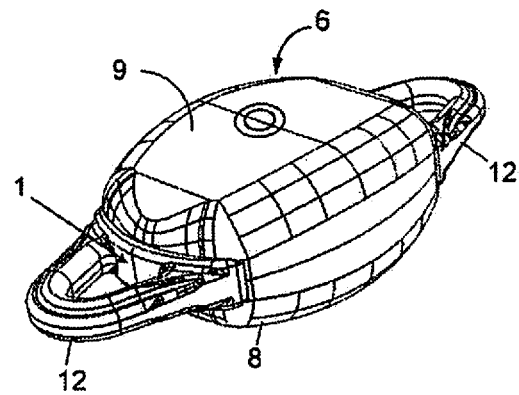
FIG. 7 is a perspective view of an example of a complete tensioning system, including the tensioner as claimed in the invention, covered by a casing.

Associated with the processing module (5) is a conditioner circuit for the strain gauge (3), a memory module for the storage of the data, a low-consumption wireless transmitter (Bluetooth LE module), a rechargeable battery to power the system, a USB port to recharge the battery, a triaxial accelerometer and a sequential pushbutton; all of these components, together with the straight central segment (11) and the angled bends (10) of the tensioner (1), being integrated in spaces executed in the interior of a rigid, lightweight casing (6) (FIG. 7), forming a compact assembly which conceals and protects the straight central segment (11) of the tensioner (1) and the processing module (5), and provides the sensor system with the necessary consistency to withstand falls and undesired impacts during its operation in the normal environment for its use.

Furthermore, the rigid casing (6) is comprised of two separate sections; the base (8), within which the tensioner (1) and the processing module (5) with all its components are assembled, and the cover (9), which presents around its rim a system of rubber seals, enabling the airtight closure of the rigid casing (6), and which is able to absorb, thanks to its elastic properties, the necessary distortion of the tensioner (1) on being subjected to tensile forces within its nominal working range.

All this considered, a sensor system is obtained which enables the measurement of the tension generated in any type of action involving traction (F) and the real-time sending of the data recorded by means of the wireless transmitter module (13) to an external device such as a smartphone or tablet for their processing by means of a specific app able to present the results to the user in real time, providing an instant feedback of the levels of average and maximum force achieved, the number of repetitions performed, the rhythm of the execution of the repetitions or their duration, among other variables of interest.

The sensor system of the invention may be anchored between two points where a tensile force (F) is generated, it being able to measure the instantaneous levels of tension both under dynamic conditions, where the sensor system moves in accordance with the action or exercise in which the tension to be measured is generated, or under static conditions, where the sensor system is anchored by one of the affixing extremities (12) of the tensioner (1), for example by means of a carabiner, to an immovable fixed point from which the tension is generated.

Figure 9:
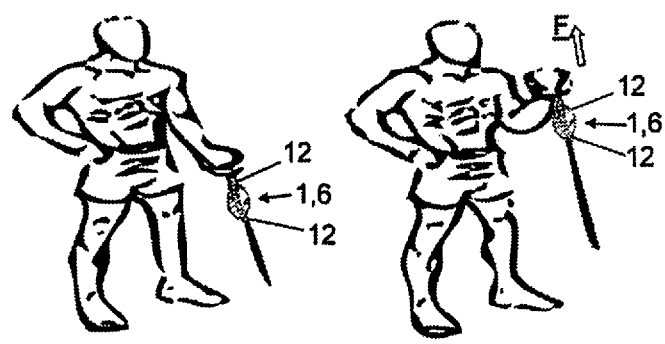
FIG. 9 portrays an example of the use of the force sensor system of the present invention, adapted to a biceps curl.

FIG. 9 portrays an example of its use in an action recorded under dynamic conditions, where the sensor system is anchored by one of the affixing extremities (12) of the tensioner (1) to one extremity of an elastic band from which the tension is generated, and to the other of the affixing extremities (12) the subject's traction handle grip is anchored. In this case, the sensor system would record the traction force which the subject is able to exert on stretching the elastic band during the biceps curl exercise.

Another example (not portrayed in the drawings) is another action recorded under static conditions where the sensor system is anchored by one of the affixing extremities (12) of the tensioner (1) to an immovable fixed point from which the tension is generated, and is anchored by the other of its affixing extremities (12) for example to one of the extremities of a chain. In this case, the sensor system would record the traction force which the subject is able to exert on tensing the free extremity of the chain.

In view of the above, the sensor of the invention features innovative and advantageous characteristics, acquiring its own identity and preferential nature with regard to the devices already in existence and with similar functions. In accordance with the invention, a wireless sensor system is proposed for the recording of tensile forces, for its application in a great variety of conventional variable resistance machines available in the physical activity and athletics sector with which exercises with different levels of tensile forces may be performed, with which advantageous functional characteristics are obtained, as the structural design of its essential components enables the obtaining of a sensor system at a reduced cost and minimum weight (<0.175 kg), and sufficiently accurate over a wide tensile range (nominal capacity: 300 kg; resolution of the measurement: <0.3 kg), further enabling a rapid, simple placement of the sensor and the real-time wireless transmission of the data to a smartphone or electronic tablet which will manage the information by means of a specific app, thus providing an effective solution to the problems arising in the current state of the art.

The object of the invention may also be used in other applications where it may be convenient to measure the tensile force exerted either by humans or by any other element exerting a force lower than the maximum limit intended for the device. As a practical example of other applications outside the context of physical exercise, it could be used for the weighing of objects.

The invention claimed is:

1. A tensile force sensor adapted for recording and monitoring of physical exercise, said tensile force sensor comprising at least one strain gauge (3), said tensile force sensor further comprising:
   a. a tensioner (1) comprising a straight central segment (11) defining a rectilinear form having a plane and a longitudinal axis, said straight central segment having a first thickness, and two angled bends (10) serving as arms set on opposing ends of said straight central segment, said angled bends forming angles offset from said plane, said arms each having a second thickness, both the central segment and two angled bends made from a hard material with predetermined constant of elasticity, each of said angled bends coupled to said straight central segment on interior ends of each of said arms, and coupled to affixing extremities at opposing ends of each of said arms; wherein said second thickness is significantly greater than said first thickness adapted to allow the straight central segment to bend under longitudinal tension forces while the arms are not appreciably bent;
   b. wherein said at least one strain gauge (3) disposed on said straight central segment (11) in such a way to monitor dimensional deformation of said straight central segment perpendicular said plane;
   wherein tensile forces applied in a force parallel said plane causes transformation of force vectors perpendicular said plane to cause said straight central segment to bend into a U-shaped distortion of the straight central segment (11), said at least one strain gauge adapted to measure the distance of elastic distortion of said straight central segment perpendicular said plane.

2. A tensile force sensor as set forth in claim 1, further comprising:
   a. a processing module (5) connected to the strain gauge (3), adapted to detect and to process the elastic distortions caused in the straight central segment (11) by the tensile forces; and
   b. a wireless transmitter module in communication with said processing module and adapted to send data concerning the elastic distortions to an external device.

3. A tensile force sensor as set forth in claim 2, further comprising an app, for mobile telephone or tablet, for processing on a processor, and presentation of the data to a user on a graphical user interface, and to save recorded results in a memory of said external device.

4. A tensile force sensor as set forth in claim 2, wherein components of the processing module (5), together with the straight central segment (11) and the angled bends (10) of the tensioner (1), are integrated in the interior of a rigid casing (6), said casing enclosing the straight central segment (11) of the tensioner (1) and the processing module (5).

5. A tensile force sensor as set forth in claim 1, wherein said affixing extremities (12) at the tensioner (1) comprise spaces adapted for anchoring of carabiners, threaded elements or grip handles, for secure attachment of said tensioner to a conventional resistance systems for physical exercise.

6. A tensile force sensor as set forth in claim 2, wherein said affixing extremities (12) at the tensioner (1) comprise spaces adapted for anchoring of carabiners, threaded elements or grip handles, for secure attachment of said tensioner.

7. A tensile force sensor as set forth in claim 3, wherein said affixing extremities (12) at the tensioner (1) comprise spaces adapted for anchoring of carabiners, threaded elements or grip handles, for secure attachment of said tensioner.

8. A tensile force sensor as set forth in claim 4, wherein said affixing extremities (12) at the tensioner (1) comprise spaces adapted for anchoring of carabiners, threaded elements or grip handles, for secure attachment of said tensioner.

9. A tensile force sensor as set forth in claim 1, wherein the tensioner (1) hard material comprises a metal alloy.

* * * * *